United States Patent [19]

Okayama et al.

[11] Patent Number: 5,665,348
[45] Date of Patent: Sep. 9, 1997

[54] CHOLESTEROL-LOWERING DRUG

[75] Inventors: Minenobu Okayama; Shuji Sato, both of Tsukuba, Japan

[73] Assignee: Hisamitsu Pharmaceutical Co, Inc., Tosu, Japan

[21] Appl. No.: 256,486

[22] PCT Filed: Jan. 11, 1993

[86] PCT No.: PCT/JP93/00022

§ 371 Date: Jul. 8, 1994

§ 102(e) Date: Jul. 8, 1994

[87] PCT Pub. No.: WO93/13781

PCT Pub. Date: Jul. 22, 1993

[30] Foreign Application Priority Data

Jan. 14, 1992 [JP] Japan .................................. 4-024531

[51] Int. Cl.$^6$ .................................................. A61K 31/785
[52] U.S. Cl. ............................. 424/78.35; 424/78.1
[58] Field of Search ........................... 424/78.35, 78.1

[56] References Cited

U.S. PATENT DOCUMENTS 2,843,573  7/1958  Melamed ............................. 526/260
3,787,474  1/1974  Daniels et al. ...................... 414/78.1
5,236,701  8/1993  St. Pierre et al. .................... 424/78.1

FOREIGN PATENT DOCUMENTS 756035    3/1971   Belgium ............................. 424/78.1
WO9118027 11/1991  WIPO ................................ 428/78.12

*Primary Examiner*—Peter F. Kulkosky
*Attorney, Agent, or Firm*—Bucknam and Archer

[57] ABSTRACT

A cholesterol-lowering drug which comprises, as the main ingredient, a non-crosslinked anion exchange resin consisting of structural units represented by the general formula (I):

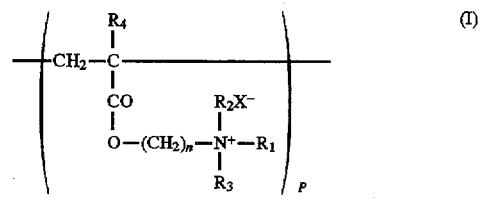

wherein $R_1$ represents a benzyl group or an alkyl group having 1 to 20 carbon atoms, $R_2$ and $R_3$ may be identical with, or different from, each other and each represent a lower alkyl group having 1 to 4 carbon atoms, $R_4$ represents a hydrogen atom or a lower alkyl group, X represents a physiologically acceptable counter ion, n is an integer of from 1 to 3, and p is an average degree of polymerization ranging from 10 to 10,000.

6 Claims, 1 Drawing Sheet

Dose-Response Curves of the Suppression of Increase in Cholesterol Level

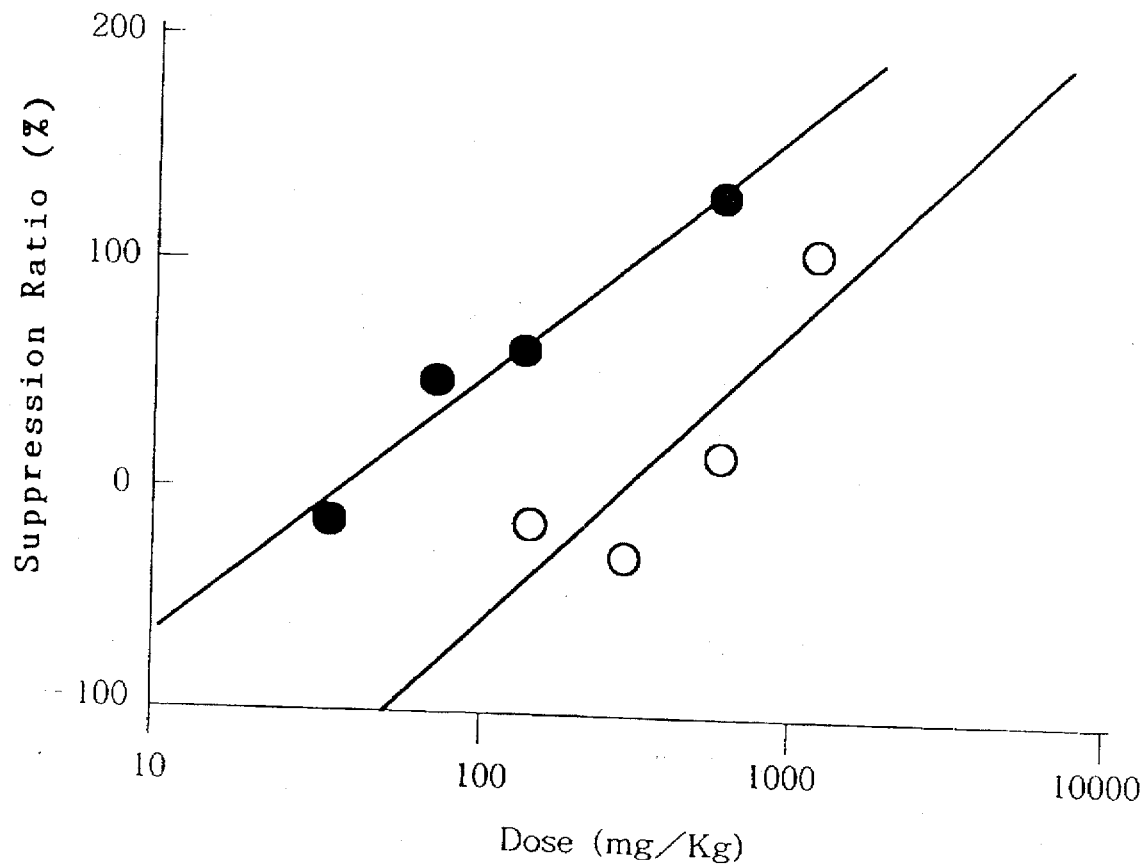
Dose-Response Curves of the Suppression of Increase in Cholesterol Level
F I G. 1

CHOLESTEROL-LOWERING DRUG

This application is a 371 of PCT/JP93/00022 filed Jan. 11, 1993.

TECHNICAL FIELD

This invention relates to a cholesterol-lowering drug containing an anion exchange resin by which a blood cholesterol level can be remarkably lowered.

BACKGROUND ART

It has been known that lowering a blood cholesterol level is effective in preventing atherosclerosis. In particular, the investigation conducted by U.S. Lipid Research Clinics Program has clarified that a decrease in blood cholesterol level correlates to the suppression of the incidence of cardiac coronary arterial diseases and that anion exchange resins are effective in preventing these diseases. Anion exchange resins which are publicly known to have been used as a cholesterol-lowering drug for lowering a blood cholesterol level, are for example cholestyramine which is a polymer of styrylmethyltrimethylammonium chloride, and a composition containing styrylmethyltrimethylammonium chloride (see U.S. Pat. Nos. 8,499,960 and 8,780,171 and Japanese Patent Laid-Open Gazette No. 10886/78). Further, a copolymer of imidazole with halomethyloxysilane, having a higher efficacy than cholestyramine, has been reported as another example (see Japanese Patent Laid-Open Gazette No. 124819/90). Furthermore, Japanese Patent Laid-Open Gazette No. 212505/90 disclose an acrylic polymer containing a quaternarized alkylammonium and a composition comprising the polymer as still other examples. However, the exchange capacity (from 1.98 to 3.66 meq Cl$^-$/g) disclosed in this Gazette cannot be thought to be sufficiently large as compared with that of cholestyramine (2.9 meq Cl$^-$/g; see U.S. Pat. No. 3,780,171). The compound disclosed in the Japanese Patent Laid-Open Gazette No. 212505/90 cited above involves a crosslinking unit as an essential constituent factor. Accordingly, this Gazette has neither disclosed nor suggested that non-crosslinked acrylic polymers disclosed in the present invention have an effect of lowering a cholesterol level.

It is believed that these anion exchange resins adsorb and fix bile acids thereto and thus promote the catabolism of cholesterol into bile acids to thereby lower a blood cholesterol level as will be discussed in greater detail hereinafter.

Bile acids are synthesized from cholesterol serving as a precursor thereof in the liver, secreted from the common bile duct into the intestinal tract, absorbed together with fat-soluble substances and then recovered into the liver, thus circulating through the bowels and the liver. Therefore, bile acids are present in a fixed amount in the cycle called the enterohepatic circulation without their systemic circulation (bile acid pool). When bile acids are bonded to an anion exchange resin in the intestinal tract and evacuated, the amount of bile acids pooled is reduced. As a result, cholesterol 7 α-hydroxylase is activated in hepatic cells and thus bile acids are biosynthesized. Then the cholesterol concentration in the liver is lowered. To make up for the decreased cholesterol concentration, LDL (low density lipoprotein) receptor appears on hepatic cell membranes and thus LDL cholesterol in the blood is recovered or withdrawn into the liver. As a result, the blood cholesterol level is lowered. It is believed that the anion exchange resin exerts the effect of lowering cholesterol level through the mode of action as described above.

Typical of drugs for treating hypercholesterolemia which are known today are as follows. For example, cholestyramine has been widely used in a clinic as a priority drug for treating familial hypercholesterolemia; however, it has a disadvantage that it adsorbs fat-soluble vitamins under the influence of hydrophobic interaction, thereby making it necessary to supply fat-soluble vitamins such as vitamins K and D to make up for the poverty thereof in the case of the prolonged administration of cholestyramine. In addition, conventional cholesterol-lowering drugs including cholestyramine preparations are inconvenient in that they should be suspended before use. Cholestyamine has another disadvantage that a patient is forced to take a large dose (8 to 16 g per day) because of its poor capability of adsorbing bile acids, thus inflicting a burden to the patient. Furthermore, it is known that a cross-linked polymer is expanded in volume through swelling. This is sometimes clinically observed as side effects including abdominal swelling and constipation. Furthermore, a still another disadvantage is that some patients will not take the drug as directed by the doctor because of said problems raised at the time of administration of the above conventional drugs.

As an existing technique for solving the above-mentioned problems, Sugii et al. of Kumamoto University introduced an ω-oxobutyl chain as a spacer between an aliphatic quaternary ammonium salt and a main polystyrene chain and thus improved the accessibility of bile acids to an ion exchange group and the hydrophobic interaction of the spacer to thereby enhance the adsorption affinity, thus increasing the amount of bile acids discharged in feces [see J. Pharmacobio-Dyn., 13, 130–135 (1990)]. However, this ion exchange resin has a still low bile acid adsorptivity and therefore it exerts only an insufficient effect of lowering a blood cholesterol level.

On the other hand, existing water-soluble quaternarized polymers such as cationized cellulose will highly irritate the mucosae when used and thus they do not satisfy the practical usefulness as a drug for internal use.

It is an object of the present invention to provide a cholesterol-lowering drug which can be easily taken in the form of, for example, tablets, granules and capsules, which relieves side effects such as abdominal swelling and constipation experienced in the conventional cholesterol-lowering drugs containing cross-linked ion exchange resins, which overcomes their disadvantages of adsorbing fat-soluble vitamins and forcing a patient to have a large burden at the time of their administration and which eliminates the inconvenience that they must be suspended before use.

DISCLOSURE OF THE INVENTION

The present inventors have conducted extensive studies in order to solve the abovementioned problems. As a result, they have found: (1) that by replacing an alkyl group of an aliphatic quaternary ammonium salt of an anion exchange resin by, for example, a long-chain alkyl group or a benzyl group, the selective adsorption of bile acids can be enhanced and the mucosal irritation can be relieved as compared with the existing anion exchange resins; (2) that by using a linear resin, the effective amount of bile acids adsorbed per unit weight of resin can be increased; and (3) that the larger the amount of bile acids adsorbed per unit weight of resin is, the more the blood cholesterol level is reduced. The present invention has been completed based on these findings.

The present invention relates to a cholesterol-lowering drug which comprises a resin consisting of structural units represented by the following general formula (I) as the main ingredient and more particularly it relates to a non-cross-linked anion exchange resin consisting of structural units represented by the general formula (I)

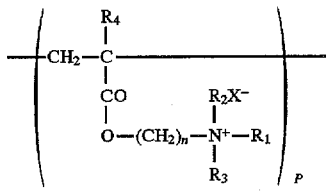

wherein $R_1$ represents a benzyl group or an alkyl group having 1 to 20 carbon atoms, $R_2$ and $R_3$ may be identical with, or different from, each other and each represent a lower alkyl group having 1 to 4 carbon atoms, $R_4$ represents a hydrogen atom or a lower alkyl group, X represents a physiologically acceptable counter ion, n is from 1 to 3, and p is an average degree of polymerization ranging from 10 to 10,000.

Now, the above general formula (I) will be described in greater detail. $R_1$ represents a benzyl group or a linear or branched alkyl group having 1 to 20 carbon atoms, i.e., ranging from methyl to eicosyl; $R_2$ and $R_3$ may be the same as, or different from, each other and each represent a linear or branched lower alkyl group having 1 to 4 carbon atoms selected from among methyl, ethyl, propyl and butyl groups; $R_4$ represents a hydrogen atom or a linear or branched lower alkyl group having 1 to 4 carbon atoms selected from among methyl, ethyl, propyl and butyl groups; the physiologically acceptable counter ion represented by $X^-$ is illustrated by the anion of a bicarbonate, carbonate, formate, acetate, sulfate, propionate, malonate, succinate, fumarate, ascorbate, sulfonate, phosphate, halide and glucuronate or amino acid typically represented by aspartic acid or glutamic acid. Among these counter ions, the anion of a sulfate or phosphate, or a halide ion such as $Cl^-$ or $Br^-$ is particularly preferable.

Now a typical example of a production process of the present invention will be described. For example, a general method wherein a benzyl group is introduced as $R_1$ may be effected in the following manner. An unsaturated N,N-dimethylamine such as acryloyloxyethyl-N,N-dimethylamine or methacryloyloxyethyl-N,N-dimethylamine is reacted with an aralkyl halide such as benzyl chloride or benzyl bromide in an organic solvent such as acetone, methanol, ethanol, diethyl ether or isopropyl ether. The quaternary monomer thus obtained is subjected to free-radical polymerization in accordance with the conventional method in water or a polar solvent such as ethanol or methanol in the presence of a free-radical initiator such as azobisisobutyronitrile (AIBN) or an ammonium persulfate redox initiator (for example, ammonium persulfate/sodium hydrogensulfite). The reaction product is precipitated from an appropriate organic solvent such as acetone or dioxane and dried by air-drying, vacuum-drying, spray-drying or freeze-drying to thereby give an anion exchange resin.

When the anion exchange resin which is the compound of the present invention is to be used in therapeutics, it is generally employed in the form of a drug composition. Thus a drug composition is prepared by incorporating the anion exchange resin with pharmacologically acceptable vehicles or excipients.

The drug composition of the present invention can be formulated into, for example, tablets, granules, dusts, capsules, syrups, emulsions, suspensions or solutions by a publicly or well known method. For example, a solid preparation in the form of tablets or granules can be obtained by appropriately blending with the excipients, for example, sugars such as lactose, sucrose, glucose, mannitol or sorbitol, starches such as corn starch, potato starch or dextrin, microcrystalline cellulose, gum arabic, dextrin, pullulan, light silicic anhydride, aluminum silicate, magnesium metasilicate aluminate, magnesium silicate, calcium phosphate, calcium carbonate or calcium sulfate, disintegrating agents such as carboxymethylcellulose, carboxymethylcellulose sodium, carboxymethylcellulose calcium, hydroxypropylcellulose, crystalline cellulose, ethylcellulose, carboxymethylstarch sodium or croscarmellose sodium, binders such as polyvinylpyrrolidone, polyvinyl alcohol or hydroxypropylcellulose, lubricating agents such as talc, stearic acid, magnesium stearate or calcium stearate, and other components such as polyethylene glycols, propylene glycol and coloring matters.

To formulate preparations for use in the capsuled form, there may be appropriately blended together base materials for a hard or soft capsule which are gelatin, glycerol, sorbitol, propylene glycol, sucrose, a plasticizer such as gum arabic, a pigment and a coloring matter such as titanium dioxide, a preservative such as methyl, ethyl or propyl p-hydroxybenzoate (parabens), perfume and other excipients.

To formulate preparations in the form of syrups, emulsions, suspensions and solutions, there may be blended together solubilizers or emulsifiers such as water, ethanol, nonionic surfactants such as glycerol, sorbitol, polyethylene glycol, propylene glycol, glycerol monostearate, polyoxyl stearate, lauromacrogol, sorbitan oleate, polysorbate 80 and sucrose fatty acid esters, anionic surfactants such as stearyltriethanol-amine and sodium lauryl sulfate, cationic surfactants such as benzalkonium chloride and benzethonium chloride, ampholytic surfactants such as lecithin, suspending agents or dispersing agents such as the nonionic, anionic and cationic surfactants as cited above, polyvinyl compounds such as polyvinyl alcohol and polyvinylpyrrolidone, cellulose derivatives such as carboxymethylcellulose sodium, methylcellulose, hydroxymethylcellulose, hydroxyethylcellulose, hydroxypropylcellulose and hydroxypropylmethylcellulose, other materials such as gum arabic and gelatin, thickening agents such as aluminum magnesium silicate, colloidal hydrous aluminum magnesium silicate, bentonite, kaolin and microcrystalline cellulose, preservatives such as parabens, benzalkonium chloride and benzethonium chloride, flavors and sweeteners such as fructose, invert sugars, cocoa, citric acid, ascorbic acid and fruit juices, and other excipients.

Each preparation thus obtained is formulated into a unit dose form containing from 0.01 to 8.0 g of the anion exchange resin obtained by the present invention.

This preparation can be administered to a patient in a dose of from 0.1 to 9 g/day, preferably from 0.1 to 5 g/day, once to thrice per day. It is necessary to repetitively administer the preparation for at least a period of time sufficient for causing a decrease in the serum cholesterol level.

BRIEF DESCRIPTION OF THE DRAWING

FIG. 1 shows does-response curves of the suppression of increase in cholesterol level wherein closed circles represent the data of the resin of Example 3 while open circles the data of cholestyramine.

BEST MODE FOR CARRYING OUT THE INVENTION

To further illustrate the present invention in greater detail and to clarify the effects of the same, the following Examples (Examples, Formulation Examples, Test Examples) will be given. However, it is to be understood that the present invention is not restricted thereto.

EXAMPLE 1

Into a two-necked flask provided with a reflux condenser and a dropping funnel were introduced 85.9 g (0.6 mol) of acryloyloxyethyl-N,N-dimethylamine, 160 g of acetone and 0.1 g of hydroquinone monomethyl ether, which was employed as a polymerization inhibitor, and then mixed homogeneously. After bubbling chloromethane thereinto, the mixture was allowed to stand overnight under stirring at room temperature. Then the reaction mixture was washed with 500 ml of acetone and thus crystals of acryloyloxyethyltrimethylammonium chloride were obtained.

150 g of the crystals of acryloyloxyethyltrimethylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis(2-amidinopropane) hydrochloride was added thereto as a polymerization initiator. After effecting a reaction for about 20 hours, the reaction product was reprecipitated from acetone to thereby give an anion exchange resin.

EXAMPLE 2

Into a two-necked flask provided with a reflux condenser and a dropping funnel were introduced 94.3 g (0.6 mol) of methacryloyloxyethyl-N,N-dimethylamine, 160 g of acetone and 0.1 g of hydroquinone monomethyl ether, which was employed as a polymerization inhibitor, and then mixed homogeneously. After bubbling chloromethane thereinto, the mixture was allowed to stand overnight under stirring at room temperature. Then the reaction mixture was washed with 500 ml of acetone and thus crystals of methacryloyloxyethyltrimethylammonium chloride were obtained.

150 g of the crystals of methacryloyloxyethyltrimethylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis(2-amidinopropane) hydrochloride was added to the aqueous solution as a polymerization initiator. After effecting a reaction for about 20 hours, the reaction product was reprecipitated from acetone to thereby give an anion exchange resin.

EXAMPLE 3

Into a two-necked flask provided with a reflux condenser and a dropping funnel were introduced 85.9 g (0.6 mol) of acryloyloxyethyl-N,N-dimethylamine, 160 g of acetone and 0.1 g of hydroquinone monomethyl ether, which was employed as a polymerization inhibitor, and then mixed homogeneously. After dropping 75.9 g (0.6 mol) of benzyl chloride into the homogeneous mixture within about 15 minutes, the mixture was allowed to stand overnight under stirring at room temperature. Then the reaction mixture was washed with 500 ml of acetone and thus crystals of acryloyloxyethyl-N,N-dimethylbenzylammonium chloride were obtained.

150 g of the crystals of acryloyloxyethyl-N,N-dimethylbenzylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis(2-amidinopropane) hydrochloride was added thereto as a polymerization initiator. After effecting a reaction for about 20 hours, the reaction product was reprecipitated from acetone to thereby give an anion exchange resin.

EXAMPLE 4

Into a two-necked flask provided with a reflux condenser and a dropping funnel were introduced 94.3 g (0.6 mol) of methacryloyloxyethyl-N,N-dimethylamine, 152 g of acetone and 0.1 g of hydroquinone monomethyl ether, which was employed as a polymerization inhibitor, and then mixed homogeneously. After dropping 75.9 g (0.6 mol) of benzyl chloride thereinto within about 15 minutes, the mixture was allowed to stand overnight under stirring at room temperature. Then the reaction mixture was washed with 500 ml of acetone to obtain crystals of methacryloyloxyethyl-N,N-dimethylbenzylammonium chloride.

150 g of the crystals of methacryloyloxyethyl-N,N-dimethylbenzylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis(2-amidinopropane) hydrochloride was added to the aqueous solution as a polymerization initiator. After effecting a reaction for about 20 hours, the reaction product was reprecipitated from acetone to thereby give an anion exchange resin.

EXAMPLE 5

Into a two-necked flask provided with a reflux condenser and a dropping funnel were introduced 5.9 g (0.8 mol) of acryloyloxyethyl-N,N-dimethylamine, 184 g of acetone and 0.1 g of hydroquinone monomethyl ether, which was employed as a polymerization inhibitor, and mixed homogeneously. After dropping 72.4 g (0.8 mol) of 1-chlorohexane thereinto within about 15 minutes, the mixture was allowed to stand overnight under stirring at room temperature. Then the reaction mixture was washed with 500 ml of acetone and thus crystals of acryloyloxyethyl-N,N-dimethylhexylammonium chloride were obtained.

150 g of the crystals of acryloyloxyethyl-N,N-dimethylhexylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis(2-amidinopropane) hydrochloride was added thereto as a polymerization initiator. After effecting a reaction for about 20 hours, the reaction product was reprecipitated from acetone to thereby give an anion exchange resin.

EXAMPLE 6

Into a two-necked flask provided with a reflux condenser and a dropping funnel were introduced 94.3 g (0.6 mol) of methacryloyloxyethyl-N,N-dimethylamine, 155 g of acetone and 0.1 g of hydroquinone monomethyl ether, which was employed as a polymerization inhibitor, and mixed homogeneously. After dropping 72.4 g (0.6 mol) of 1-chlorohexane thereinto within about 15 minutes, the mixture was allowed to stand overnight under stirring at room temperature. Then the reaction mixture was washed with 500 ml of acetone and thus crystals of methacryloyloxyethyl-N,N-dimethylhexylammonium chloride were obtained.

150 g of the crystals of methacryloyloxyethyl-N,N-dimethylhexylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis(2-amidinopropane) hydrochloride was added thereto as a polymerization initiator. After effecting a reaction for about 20 hours, the reaction product was reprecipitated from acetone to thereby give an anion exchange resin.

EXAMPLE 7

Into a two-necked flask provided with a reflux condenser and a dropping funnel were introduced 85.9 g (0.6 mol) of acryloyloxyethyl-N,N-dimethylamine, 86 g of isopropyl ether and 0.1 g of hydroquinone monomethyl ether, which was employed as a polymerization inhibitor, and mixed homogeneously. After dropping 149.5 g (0.6 mol) of 1-bromododecane thereinto within about 15 minutes, the mixture was allowed to stand overnight under stirring at room temperature. Then the reaction mixture was washed with 500 ml of isopropyl ether and thus crystals of acryloyloxyethyl-N,N-dimethyldodecylammonium bromide were obtained.

150 g of the crystals of acryloyloxyethyl-N,N-dimethyldodecylammonium bromide thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis (2-amidinopropane) hydrochloride was added thereto as a polymerization initiator. After effecting a reaction for about 20 hours, the reaction product was reprecipitated from acetone to thereby give an anion exchange resin.

EXAMPLE 8

Into a two-necked flask provided with a reflux condenser and a dropping funnel were introduced 94.3 g (0.6 mol) of methacryloyloxyethyl-N,N-dimethylamine, 78 g of isopropyl ether and 0.1 g of hydroquinone monomethyl ether, which was employed as a polymerization inhibitor, and mixed homogeneously. After dropping 149.5 g (0.6 mol) of 1-bromododecane thereinto within about 15 minutes, the mixture was allowed to stand overnight under stirring at room temperature. Then the reaction mixture was washed with 500 ml of isopropyl ether to obtain crystals of methacryloyloxyethyl-N,N-dimethyldodecylammonium bromide.

150 g of the crystals of methacryloyloxyethyl-N,N-dimethyldodecylammonium bromide thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis (2-amidinopropane) hydrochloride was added thereto as a polymerization initiator. After effecting a reaction for about 20 hours, the reaction product was reprecipitated from acetone to thereby give an anion exchange resin.

EXAMPLE 9

Into a two-necked flask provided with a reflux condenser and a dropping funnel were introduced 85.9 g (0.6 mol) of acryloyloxyethyl-N,N-dimethylamine, 63 g of isopropyl ether and 0.1 g of hydroquinone monomethyl ether, which was employed as a polymerization inhibitor, and mixed homogeneously. After dropping 173.4 g (0.6 mol) of 1-chlorooctadecane thereinto within about 15 minutes, the mixture was allowed to stand overnight under stirring at room temperature. Then the reaction mixture was washed with 500 ml of isopropyl ether and thus crystals of acryloyloxyethyl-N,N-dimethyloctadecylammonium chloride were obtained.

150 g of the crystals of acryloyloxyethyl-N,N-dimethyloctadecylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis (2-amidinopropane) hydrochloride was added to the aqueous solution as a polymerization initiator. After effecting a reaction for about 20 hours, the reaction product was reprecipitated from acetone to thereby give an anion exchange resin.

EXAMPLE 10

Into a two-necked flask provided with a reflux condenser and a dropping funnel were introduced 94.3 g (0.6 mol) of methacryloyloxyethyl-N,N-dimethylamine, 54 g of isopropyl ether and 0.1 g of hydroquinone monomethyl ether, which was employed as a polymerization inhibitor, and mixed homogeneously. After dropping 173.4 g (0.8 mol) of 1-chlorooctadecane thereinto within about 15 minutes, the mixture was allowed to stand overnight under stirring at room temperature. Then the reaction mixture was washed with 500 ml of isopropyl ether and thus crystals of methacryloyloxyethyl-N,N-dimethyloctadecylammonium chloride were obtained.

150 g of the crystals of methacryloyloxyethyl-N,N-dimethyloctadecylammonium chloride thus obtained were dissolved in 280 g of purified water in a three-necked separable flask provided with a reflux condenser and the flask was purged with nitrogen for 5 hours. While maintaining the reaction temperature at 65° C., 0.01 g of 2,2'-azobis (2-amidinopropane) hydrochloride was added thereto as a polymerization initiator. After effecting a reaction for about 20 hours, the reaction product was reprecipitated from acetone to thereby give an anion exchange resin.

EXAMPLE 11

(Comparative Example)

150 g of the crystals of acryloyloxyethyltrimethylammonium chloride obtained in Example 1 and 2.6 g (0.3 mol %) of polyethylene glycol 10000 bismethacrylate (hereinafter referred to simply as PEG-10000BM) were dissolved in 280 g of purified water in a three-necked separable flask provided with a reflux condenser. Then the flask was purged with nitrogen for 5 hours. While maintaining the reaction temperature at 65° C., 0.01 g of 2,2'-azobis (2-amidinopropane) hydrochloride was added thereto as a polymerization initiator. After effecting a reaction for about 20 hours, the reaction product was reprecipitated from acetone. About 50 g of the precipitate were allowed to stand in 5000 ml of purified water overnight. Then the gel thus obtained was freeze-dried to thereby give an anion exchange resin of from 100-mesh to 200-mesh in grain size.

EXAMPLE 12

(Comparative Example)

Substituting 150 g of methacryloyloxyethyltrimethylammonium chloride in crystal form obtained in Example 2 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 13

(Comparative Example)

Substituting 150 g of acryloyloxyethyl-N,N-dimethylbenzylammonium chloride in crystal form obtained in Example 3 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 14

(Comparative Example)

Substituting 150 g of methacryloyloxyethyl-N,N-dimethylbenzylammoniun chloride in crystal form obtained in Example 4 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 15

(Comparative Example)

Substituting 150 g acryloyloxyethyl-N,N-dimethylhexylammonium chloride in crystal form obtained in Example 5 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 16

(Comparative Example)

Substituting 150 g of methacryloyloxyethyl-N,N-dimethylhexylammonium chloride in crystal form obtained in Example 6 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 17

(Comparative Example)

Substituting 150 g of acryloyloxyethyl-N,N-dimethyldodecylammonium bromide in crystal form obtained in Example 7 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 18

(Comparative Example)

Substituting 150 g of methacryloyloxyethyl-N,N-dimethyldodecylammonium bromide in crystal form obtained in Example 8 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 19

(Comparative Example)

Substituting 150 g of acryloyloxyethyl-N,N-dimethyloctadecylammonium chloride in crystal form obtained in Example 9 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 20

(Comparative Example)

Substituting 150 g of methacryloyloxyethyl-N,N-dimethyloctadecylammonium chloride in crystal form obtained in Example 10 for the acryloyloxyethyltrimethylammonium chloride used in Example 11, as one of the raw materials, and using 2.6 g (0.3 mol %) of PEG-10000BM as the other raw material, the procedure of Example 11 was followed thereby to obtain an anion exchange resin having a 100 to 200-mesh grain size.

EXAMPLE 21

Into a two-necked flask provided with a reflux condenser and a dropping funnel were introduced 85.9 g (0.6 mol) of acryloyloxyethyl-N,N-dimethylamine, 160 g of acetone and 0.1 g of hydroquinone monomethyl ether, which was employed as a polymerization inhibitor, and then mixed homogeneously. After dropping 75.9 g (0.6 mol) of benzyl chloride thereinto within about 15 minutes, the mixture was allowed to stand overnight under stirring at room temperature. Then the reaction mixture was washed with 500 ml of acetone to obtain crystals of acryloyloxyethyl-N,N-dimethylbenzylammonium chloride.

150 g of the crystals of acryloyloxyethyl-N,N-dimethylbenzylammonium chloride thus obtained were dissolved in 280 g of purified water in a three-necked separable flask provided with a reflux condenser and the flask was purged with nitrogen for 5 hours under stirring and heating at 40° C. While maintaining the reaction temperature at 40° C., 0.03 g of ammonium. persulfate and 0.015 g of sodium hydrogensulfite were added thereto as polymerization initiators. After effecting a reaction for about 20 hours, the reaction product was reprecipitated from acetone to thereby give an anion exchange resin.

Examples of formulation of preparations of the present invention will be given hereunder.

Formulation Example 1

A preparation to be provided in the form of tablets can be prepared by a process which will be described in detail hereunder. Namely, 1500 g of polyacryloyloxyethyl-N,N-dimethylbenzylammonium chloride produced in Example 21, which had been dressed to obtain 200-50 mesh granules, preferably through 100-80 mesh granules, 250 g of microcrystalline cellulose, 350 g of lactose, 375 g of carboxymethylcellulose calcium and 25 g of magnesium stearate were mixed together and molded under a tableting pressure of from 0.5 to 1.5 t, preferably 1 t, to thereby give tablets each weighing 130 to 350 mg, preferably 250 mg, and having a diameter of from 5 to 9 mm, preferably 6 mm.

Formulation Example 2

A preparation to be provided in the form of tablets can be prepared by a process which will be described in detail hereunder. Namely, 1500 g of polyacryloyloxyethyl-N,N-dimethylbenzylammonium chloride produced in Example 21 were dissolved in 30 l of 50% aqueous ethanol to thereby give a spraying solution. Separately, 600 g of microcrystalline cellulose and 375 g of carboxymethylcellulose calcium were weighed into a fluidized bed granulator. While blowing a hot air stream at 50° to 90° C., preferably 70° C., the spraying solution was sprayed from two fluid nozzles, followed by drying. To the powdery matter thus obtained was added magnesium stearate. Then tablets were produced in the same manner as in Formulation Example 1.

Formulation Example 3

A preparation to be provided in the form of granules can be prepared by a process which will be described in detail hereunder. Namely, 1500 g of polyacryloyloxyethyl-N,N-dimethylbenzylammonium chloride produced in Example 21 were dissolved in 5 l of 50% aqueous ethanol to thereby give a binding solution. Separately, 8000 g of microcrystalline cellulose, 200 g of carboxymethylcellulose calcium and 3800 g of ethylcellulose were weighed, mixed in a kneader and extruded from a screen to thereby give granules. The granules thus obtained were hot air-dried to thereby give a granular preparation.

Formulation Example 4

A preparation to be provided in the form of tablets can be prepared by a process described in detail hereunder. Namely, 1500 g of polyacryloyloxyethyl-N,N-dimethylbenzylammonium chloride produced in Example 21, which had been dressed to obtain 200-50 mesh granules, preferably 200-80 mesh granules, 17 g of light silicic acid anhydride and 133 g of lactose were mixed together, compressed under a pressure of from 50 to 160 kg/cm$^2$, preferably 80 kg/cm$^2$ ground and dressed through a 20-mesh sieve. To 1200 g of fine granules thus obtained were added 6 g of magnesium stearate. Then the mixture was molded under a tableting pressure of from 0.5 to 2.0 t, preferably 1.2 t, to thereby give tablets each weighing 200 to 600 mg, preferably 490 mg, and having a major axis length of from 4 to 16 mm, preferably 14.5 mm and a thickness of from 2 to 9 mm, preferably 6 mm.

The resins (compounds) of these Examples had a remarkably high degree of saturation of adsorption of bile acids, thus proving that they had higher affinities for bile acids. In a cholesterol increase inhibition test on rabbits, these compounds also exhibited remarkable inhibition effects.

Further, each of these compounds had an acute toxicity of 4000 mg/kg or above, which indicates that they are highly safe compounds.

To illustrate the present invention specifically, the following Test Examples will be given.

Test Example 1

Bile acid adsorption test

The ingredients of a model human bile acid salt composition which are shown in Table 1 were homogeneously mixed and then precisely weighed. 50 ml of purified water, measured accurately, were added thereto to thereby give mixtures corresponding to concentrations of 0.5, 0.6, 0.7, 0.8, 0.9, 1.0, 1.25, 1.5, 1.75, 2.0, 3.0 and 4.0 mM. In each solution, 20 mg of a resin was incubated for 12 hours. Then free bile acids were separated with the use of an ultrafiltration membrane and a membrane filter and the concentration of the free bile acids was measured by an enzymatic method (Bile Acid Test WAKO). Thus the amount of bile acids adsorbed by the resin was calculated and the saturated amount of bile acids adsorbed per unit weight of resin was determined by Langmuir's plotting. Further, the half-saturation concentration and Hill coefficient were determined by Hill's plotting. Thus the affinity for bile acids and synergistic effect of the adsorption sites were determined. Tables 2 and 3 show the results.

TABLE 1

Model human bile acid salt composition

| Bile acid salt | Amt. (g) | % |
|---|---|---|
| sodium taurocholate | 1.13 | 8.1 |
| sodium glycocholate | 3.28 | 23.4 |
| sodium taurodeoxycholate | 0.74 | 5.3 |
| sodium glycodeoxycholate | 2.91 | 20.8 |
| sodium taurochenodeoxycholate | 1.77 | 12.6 |
| sodium glycochenodeoxycholate | 4.17 | 29.8 |

TABLE 2

Bile acid adsorption performance list

| No. | $R_1$ | $R_2$ | $R_3$ | $R_4$ | Cross-linking agent | Sat. of adsorption | half-sat. conc. | Hill coef. |
|---|---|---|---|---|---|---|---|---|
| 1 | $CH_3$ | $CH_3$ | $CH_3$ | H | none | 6.03 | 0.120 | 0.9 |
| 2 | $CH_3$ | $CH_3$ | $CH_3$ | $CH_3$ | " | 4.51 | 0.017 | 0.9 |
| 3 | Benzyl | $CH_3$ | $CH_3$ | H | " | 5.02 | 0.170 | 0.5 |
| 4 | Benzyl | $CH_3$ | $CH_3$ | $CH_3$ | " | 4.03 | 0.151 | 0.4 |
| 5 | $C_6H_{13}$ | $CH_3$ | $CH_3$ | H | " | 5.33 | 0.270 | 0.3 |
| 6 | $C_6H_{13}$ | $CH_3$ | $CH_3$ | $CH_3$ | " | 3.83 | 0.012 | 1.0 |
| 7 | $C_{12}H_{25}$ | $CH_3$ | $CH_3$ | H | " | 2.74 | 0.058 | 0.4 |
| 8 | $C_{12}H_{25}$ | $CH_3$ | $CH_3$ | $CH_3$ | " | 1.24 | 0.006 | 1.0 |
| 9 | $C_{18}H_{37}$ | $CH_3$ | $CH_3$ | H | " | 2.80 | 0.089 | 0.4 |
| 10 | $C_{18}H_{37}$ | $CH_3$ | $CH_3$ | $CH_3$ | " | 1.30 | 0.030 | 1.0 |

The saturation of adsorption, which is expressed in mmol/g, and the half-saturation concentration, which is expressed in mmol/l, indicate respectively the adsorption capacity and adsorption affinity for bile acids. The Hill coefficient indicates the synergism of the adsorption sites.

Figures in the leftmost column indicate Example Nos.

TABLE 3

Bile acid adsorption performance
(when cross-linking unit is present)

| No. | $R_1$ | $R_2$ | $R_3$ | $R_4$ | Cross-linking agent | Sat. of adsorption | half-sat. conc. | Hill coef. |
|---|---|---|---|---|---|---|---|---|
| 11 | $CH_3$ | $CH_3$ | $CH_3$ | H | PEG 10000BM | 4.64 | $36 \times 10^{-3}$ | 1.4 |
| 12 | $CH_3$ | $CH_3$ | $CH_3$ | $CH_3$ | " | 4.80 | $11 \times 10^{-3}$ | 1.3 |
| 13 | Benzyl | $CH_3$ | $CH_3$ | H | " | 4.20 | $8.2 \times 10^{-3}$ | 1.2 |
| 14 | Benzyl | $CH_3$ | $CH_3$ | $CH_3$ | " | 3.26 | $6.6 \times 10^{-6}$ | 2.8 |
| 15 | $C_6H_{13}$ | $CH_3$ | $CH_3$ | H | " | 3.33 | $4.5 \times 10^{-6}$ | 3.0 |
| 16 | $C_6H_{13}$ | $CH_3$ | $CH_3$ | $CH_3$ | " | 1.53 | $2.5 \times 10^{-6}$ | 3.3 |
| 17 | $C_{12}H_{25}$ | $CH_3$ | $CH_3$ | H | " | 1.20 | $3.0 \times 10^{-6}$ | 2.8 |
| 18 | $C_{12}H_{25}$ | $CH_3$ | $CH_3$ | $CH_3$ | " | 0.60 | $2.2 \times 10^{-6}$ | 3.2 |
| 19 | $C_{18}H_{37}$ | $CH_3$ | $CH_3$ | H | " | 1.40 | $3.0 \times 10^{-6}$ | 2.1 |
| 20 | $C_{18}H_{37}$ | $CH_3$ | $CH_3$ | $CH_3$ | " | 0.65 | $1.8 \times 10^{-6}$ | 3.3 |

The saturation of adsorption, which is expressed in mmol/g, and the half-saturation concentration, which is expressed in mmol/l, indicate respectively the adsorption capacity and adsorption affinity for bile acids. The Hill coefficient indicates the synergism of the adsorption sites.

Figures in the leftmost column indicate Example Nos.

Test Example 2

Cholesterol increase inhibition test on NZW rabbits fed with cholesterol-loaded feed Using each of the resins of the Examples, a cholesterol increase inhibition test was carried out on NZW male rabbits in the following method.

NZW male rabbits weighing 1.8 kg to 2.3 kg were fed with a standard solid feed containing 0.67% of cholesterol for 1 week. Then the animals were classified into groups in such a manner that the groups were almost identical with one another in the plasma cholesterol level. During the subsequent 2 weeks, each of the resins of Examples 1 to 15 were given in a dose of 500 mg/kg to the rabbits of one specific group everyday. During this period, the standard solid feed containing 0.67% of cholesterol was continuously given at a ratio of 40 g/kg to each of the rabbits. After the end of this period of 2 weeks, the effect of inhibiting the increase in the cholesterol level of each test group was evaluated by calculating the inhibition ratio with respect to the control group (no administration of the test resin). As a control drug, cholestyramine (500 mg/kg) was employed. Table 4 shows the results.

TABLE 4

Result of cholesterol increase inhibition test

| No. | Inhibition ratio (%) |
|---|---|
| 1 | 81.2 |
| 2 | 65.2 |
| 3 | 86.6 |
| 4 | 69.5 |
| 5 | 88.9 |
| 6 | 55.1 |
| 7 | 50.5 |

TABLE 4-continued

Result of cholesterol increase inhibition test

| No. | Inhibition ratio (%) |
|---|---|
| 11 | 67.8 |
| 12 | 62.1 |
| 13 | 59.8 |
| 14 | 45.5 |
| 15 | 47.2 |
| control drug | 45.5 |

Test Example 3

Single administration toxicity test

Male Wistar-strain rats aged 7 weeks were classified into 5 groups each consisting of 8 animals in such a manner that these groups were almost identical with one another in average body weight. Then the resin of Example 3 dissolved in purified water was administered in doses of 250, 500, 1000, 2000 and 4000 mg/kg to the rats of each of the groups and the acute toxicity was monitored for 2 weeks. Table 5 shows the result including one death case.

TABLE 5

Result of single administration toxicity test

| Dose (mg/kg) | No. of death case/total test cases |
|---|---|
| 4,000 | 1/8 |
| 2,000 | 0/8 |
| 1,000 | 0/8 |
| 500 | 0/8 |
| 250 | 0/8 |

Test Example 4

Test for dosage to inhibit cholesterol increase, made on NZW rabbits fed with cholesterol-loaded feed Using the resin (compound) of Example 3, the test for dosage to inhibit cholesterol increase was made on NZW male rabbits by the following method.

NZW male rabbits weighing 1.8 kg to 2.5 kg were fed with a standard solid feed containing 0.67% of cholesterol for 1 week. Then the animals were classified into groups in such a manner that the groups were almost identical with one another in the plasma cholesterol level. During the subsequent 2 weeks, the resin of Example 3 was given to the rabbits every group in doses of 31.25 mg/kg, 62.5 mg/kg, 125 mg/kg and 500 mg/kg. On the other hand, cholestyramine used as a control drug was given in doses of 125 mg/kg, 250 mg/kg, 500 mg/kg and 1000 mg/kg.

During this period, the standard solid feed containing 0.67% of cholesterol was continuously given at a ratio of 40 g/kg to each of the rabbits.

After 2 weeks, the effect of inhibiting the cholesterol increase of each test group was evaluated by calculating the control ratio with respect to the inhibition group (no administration of the test resin). Thus a dose-response curve was prepared.

The results are shown in Table 6 and FIG. 1.

TABLE 6

Result of dosage-response test of inhibiting cholesterol increase ($ED_{50}$)

| Resin | $ED_{50}$ (mg/kg) |
|---|---|
| resin of Ex. 3 | 98.5 |
| cholestyramine | 549.4 |

Thus it has been found that the resin of Example 3 is about 5.6 times as effective as cholestyramine.

INDUSTRIAL APPLICABILITY

The resin (compound) of the present invention has a remarkably high saturability of bile acids adsorbed and is excellent in affinity therefor. Thus it will promote the removal of bile acids when used. In addition, it will exert a remarkable effect of inhibiting an increase in cholesterol level when used. Further, it is a highly safe compound without raising any problems as to toxicity. Therefore the resin of the present invention is effective in lowering cholesterol level and in treating diseases such as atherosclerosis. It can be preferably used as a cholesterol-lowering drug for lowering cholesterol level and is useful as a drug.

We claim:

1. A pharmaceutical drug composition for lowering the cholesterol content in a patient which contains as the main active component a non-crosslinked anion exchange resin, said anion exchange resin being a homopolymer obtained from the polymerization of a member selected from the group consisting of acryloyloxyethyltrimethylammonium chloride, acryloyloxyethyl-N,N-dimethylbenzyl-ammonium chloride and acryloyloxyethyl-N,N-dimethylhexylammonium chloride, the degree of polymerization being between 10 and 10,000.

2. The method of treatment of a patient suffering from high blood cholesterol level which consists of administering to said patient a cholesterol-lowering drug composition which contains a non-crosslinked anion exchange resin as the main active component, said anion exchange resin being a homopolymer obtained from the polymerization of a member selected from the group consisting of acryloyloxyethyltrimethylammonium chloride, acryloyloxyethyl-N,N-dimethylbenzylammonium chloride and acryloyloxyethyl-N,N-dimethylhexylammonium chloride, the degree of polymerization being between 10 and 10,000, said drug composition being administered in unit dosage form containing from 0.01 to 3.0 g, once to thrice a day, for at least a period of time sufficient to cause a decrease in the blood cholesterol level.

3. The pharmaceutical drug composition according to claim 1 wherein said anion exchange resin is the polymerized acryloyloxyethyl-N,N-dimethylbenzylammonium chloride, said polymerized acryloyloxyethyl N,N-dimethylbenzylammonium chloride is about 5.6 times more effective than cholestyramine in inhibiting cholesterol increase.

4. A pharmaceutical drug composition in unit dosage form according to claim 1 which contains as the active ingredient 0.01–3 g per dose of said anion exchange resin and pharmacologically acceptable carriers or excipients.

5. The pharmaceutical drug composition according to claim 4 which is in the form of a tablet, granules, a capsule, a syrup, an emulsion, a suspension or a solution.

6. The method according to claim 2, wherein said non-crossed anion exchange resin is polymerized acryloyloxyethyl N,N-dimethylbenzylammonium chloride.

* * * * *